(12) United States Patent
Whitman et al.

(10) Patent No.: US 8,636,193 B2
(45) Date of Patent: *Jan. 28, 2014

(54) STAPLE POCKET ARRANGEMENT FOR SURGICAL STAPLER

(75) Inventors: Michael P. Whitman, New Hope, PA (US); John E. Burbank, Ridgefield, CT (US)

(73) Assignee: Covidien LP, Mansfield, MA (US)

( * ) Notice: Subject to any disclaimer, the term of this patent is extended or adjusted under 35 U.S.C. 154(b) by 256 days.

This patent is subject to a terminal disclaimer.

(21) Appl. No.: 12/849,986

(22) Filed: Aug. 4, 2010

(65) Prior Publication Data

US 2011/0017799 A1   Jan. 27, 2011

Related U.S. Application Data

(63) Continuation of application No. 11/495,011, filed on Jul. 27, 2006, now Pat. No. 7,815,092.

(60) Provisional application No. 60/703,262, filed on Jul. 27, 2005.

(51) Int. Cl.
*A61B 17/068* (2006.01)

(52) U.S. Cl.
USPC .................................... 227/181.1; 227/176.1

(58) Field of Classification Search
USPC ........................... 227/19, 176.1, 180.1, 181.1
See application file for complete search history.

(56) References Cited

U.S. PATENT DOCUMENTS

| | | | |
|---|---|---|---|
| 3,494,533 A | 2/1970 | Green et al. | |
| 5,480,089 A | 1/1996 | Blewett | |
| 5,630,541 A | 5/1997 | Williamson, IV et al. | |
| 5,662,258 A | 9/1997 | Knodel et al. | |
| 6,953,138 B1 | 10/2005 | Dworak et al. | |
| 7,121,446 B2 | 10/2006 | Arad et al. | |
| 7,815,092 B2 * | 10/2010 | Whitman et al. | 227/181.1 |
| 2001/0002029 A1 * | 5/2001 | Geiste et al. | 227/19 |
| 2006/0124689 A1 * | 6/2006 | Arad et al. | 227/176.1 |

FOREIGN PATENT DOCUMENTS

EP    0 251 444 A    1/1988

OTHER PUBLICATIONS

Supplementary European Search Report—Application No. EP 06 78 8913, Date of Completion: Nov. 2, 1009; 6 pages.

* cited by examiner

*Primary Examiner* — Alexandra Elve
*Assistant Examiner* — Nathaniel Chukwurah

(57) ABSTRACT

A staple pocket arrangement on the anvil portion of a surgical stapler device includes pairs of staple pockets corresponding to each one of a plurality of staples to be closed. The staple pockets may have a generally triangular shape when viewed from above. Each respective staple leg is received at a longitudinal end of the staple pocket that provides a relatively wide target area for receiving the staple leg to eliminate or at least minimize the likelihood that a staple leg will miss the staple pocket due to, e.g., misalignment between a first jaw of the surgical stapler having the anvil and a second jaw of the surgical stapler having a cartridge configured to fire the staples. The staple pockets may be arranged in rows, each row of staple pockets being longitudinally offset from another row, such that each staple pocket in a first row of staple pockets is nested with a staple pocket from an adjacent row of staple pockets to make more efficient use of space on the anvil.

22 Claims, 7 Drawing Sheets

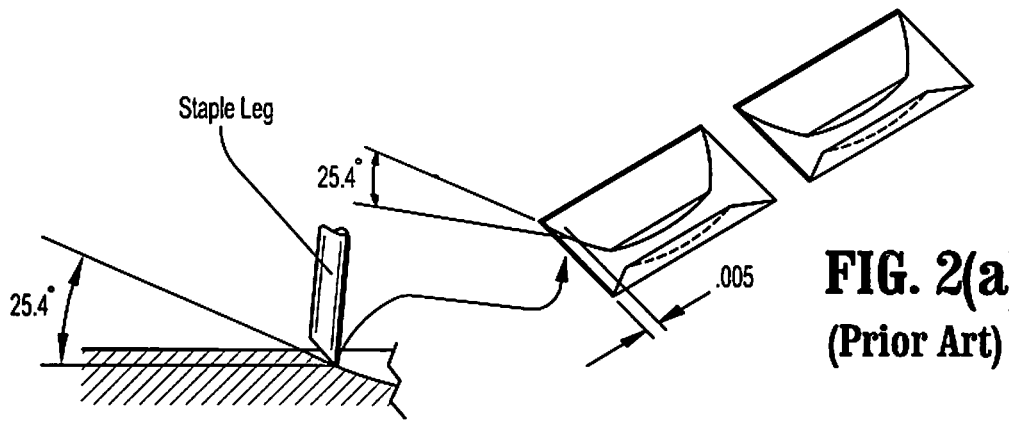
FIG. 2(a)
(Prior Art)
FIG. 2(b)
(Prior Art)
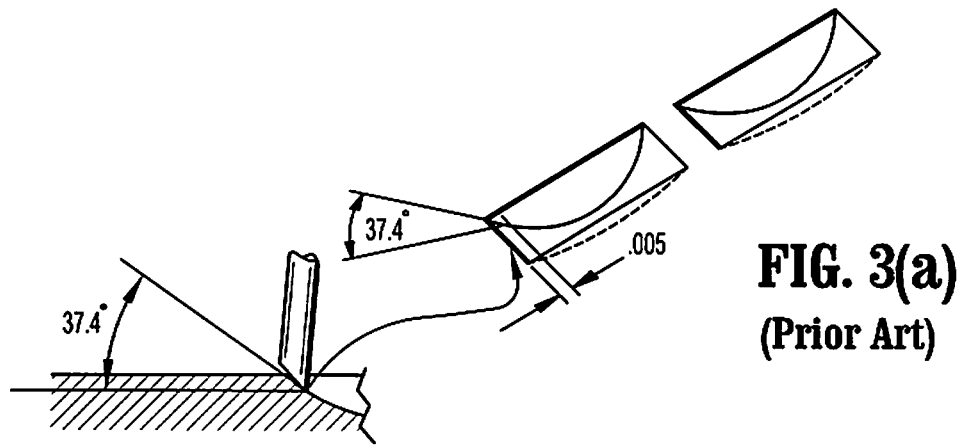
FIG. 3(a)
(Prior Art)
FIG. 3(b)
(Prior Art)

STAPLE POCKET ARRANGEMENT FOR SURGICAL STAPLER

CROSS-REFERENCE TO RELATED APPLICATIONS

This application is a Continuation Application which claims the benefit of and priority to U.S. patent application Ser. No. 11/495,011, filed Jul. 27, 2006, which claims the benefit of and priority to U.S. Provisional Patent Application Ser. No. 60/703,262, entitled "Staple Pocket Arrangement for Surgical Stapler", filed Jul. 27, 2005, each of which is expressly incorporated herein in its entirety by reference thereto.

FIELD OF THE INVENTION

The present invention relates to a staple pocket. More specifically, the present invention relates to a staple pocket arrangement for use in a surgical stapler.

BACKGROUND INFORMATION

Surgical staplers typically employ an anvil having staple pockets defined therein. Staples are pushed out of a staple cartridge through a section of tissue and against the staple pockets, the staple pockets being shaped so as to receive and progressively bend the legs of the staple into a closed position. FIG. 1 is a top view of a portion of conventional staple pocket arrangements on the anvil of a surgical stapler, e.g., a first arrangement on the upper side of the knife slot and a second arrangement on the lower side of the knife slot. Conventional staple pockets are typically rectangular in shape and maybe arranged in parallel rows.

FIG. 2(*a*) is a bottom perspective view of a conventional staple pocket arrangement on the anvil of a surgical stapler. This staple pocket arrangement employs a steep canyon wall near the floor of the canyon which changes to a shallow angle for the rest of the canyon wall. FIG. 2(*b*) is a cross-sectional view of a portion of the staple pocket illustrated in FIG. 2(*a*). FIG. 2(*b*) illustrates the staple leg being received within the staple pocket, e.g., moving in a vertical direction, and prior to the staple leg being bent into a closed position. The angle of 25.4 degrees shown in FIGS. 2(*a*) and 2(*b*) is the angle of the surface of the staple pocket relative to the plane of the anvil surface, e.g., the slope angle of the surface along which the staple leg slides when the staple leg is initially received within the staple pocket at a location about 0.005 inches from the longitudinal edge of the staple pocket.

FIG. 3(*a*) is a bottom perspective view of another conventional staple pocket arrangement on the anvil of a surgical stapler. This staple pocket arrangement employs a steep canyon wall near the floor of the canyon which changes to a shallow angle for the rest of the canyon wall. FIG. 3(*b*) is a cross-sectional view of a portion of the staple pocket illustrated in FIG. 3(*a*). FIG. 3(*b*) illustrates the staple leg being received within the staple pocket, e.g., moving in a vertical direction, and prior to the staple leg being bent into a closed position. The angle of 37.4 degrees shown in FIGS. 3(*a*) and 3(*b*) is the angle of the surface of the staple pocket relative to the plane of the anvil surface, e.g., the slope angle of the surface along which the staple leg slides when the staple leg is initially received within the staple pocket at a location about 0.005 inches from the longitudinal edge of the staple pocket.

FIG. 4 is a top view of a portion of another conventional staple pocket arrangement on the anvil of a surgical stapler. In this arrangement, there are three longitudinal rows of the staple pockets located on each side of the knife slot.

One problem that may be encountered by conventional surgical staple pocket arrangements is that the staple pockets have sharp internal corners that may contribute to snagging or stalling the staple leg of a staple as the staple leg is progressively moved through the staple pocket. Another problem that may be encountered by conventional surgical staple pocket arrangements is that the staple pockets have a narrow capture area, such that staples that are slightly mis-aligned relative to the staple pockets may miss the pocket. Another problem that may be encountered by conventional surgical staple pocket arrangements is that the staple pockets may have too shallow a slope spread over a broad area so that incoming staple legs do not encounter a sufficiently steep slide angle, thereby causing the staple legs to stall and buckle.

SUMMARY

According to an example embodiment of the present invention, a staple pocket arrangement on the anvil portion of a surgical stapler device includes pairs of staple pockets corresponding to each one of a plurality of staples to be closed. The pair of staple pockets may be arranged along a center line. A distal staple pocket may be provided for receiving and closing a distal-most leg of a staple, and a proximal staple pocket may be provided for receiving and closing a proximal-most leg of a staple. The distal staple pocket may be a mirror image of the proximal staple pocket.

The staple pockets may have a generally triangular shape when viewed from above. Each respective staple leg is received at a longitudinal end of the staple pocket that provides a relatively wide target area for receiving the staple leg to eliminate or at least minimize the likelihood that a staple leg will miss the staple pocket due to, e.g., misalignment between a first jaw of the surgical stapler having the anvil and a second jaw of the surgical stapler having a cartridge configured to fire the staples. Furthermore, each of the staple pockets is narrower at its opposite end, e.g., the end at which the staple leg emerges after being formed into an arc by the curved canyon floor of the staple pocket. The staple pocket 110 may provide canyon walls, e.g., along which a staple leg is guided, that are steeply angled for the entire wall so that the staple leg travels toward and along the center of the canyon and then up and out the narrow end of the canyon. The floor of the canyon may have a generally smooth and continuous curvature which provides, during bending of the staple leg, sufficiently large radii of curvature so as to eliminate or at least minimize tight corners that may snag or impede staple legs that are moving along the surface.

Each staple pocket in a first row of staple pockets may be nested with a staple pocket from an adjacent row of staple pockets. In this manner, when each row of staple pockets is longitudinally offset from another row, e.g., by approximately one half of the pocket-pair (or staple) center-to-center pitch, the proximal staple pocket of a first row nests with a distal staple pocket of a second row. The staple pocket arrangement may be more tolerant of poorly aimed staples, may make more efficient use of space on the anvil and may be less likely to cause a staple jam or buckling of the staple leg.

BRIEF DESCRIPTION OF THE DRAWINGS

FIG. 2(*a*) is a bottom perspective view of a conventional staple pocket arrangement on the anvil of a surgical stapler;

FIG. 2(b) is a cross-sectional view of a portion of the staple pocket illustrated in FIG. 2(a);

FIG. 3(a) is a bottom perspective view of another conventional staple pocket arrangement on the anvil of a surgical stapler;

FIG. 3(b) is a cross-sectional view of a portion of the staple pocket illustrated in FIG. 3(a);

DETAILED DESCRIPTION

Figure 1:
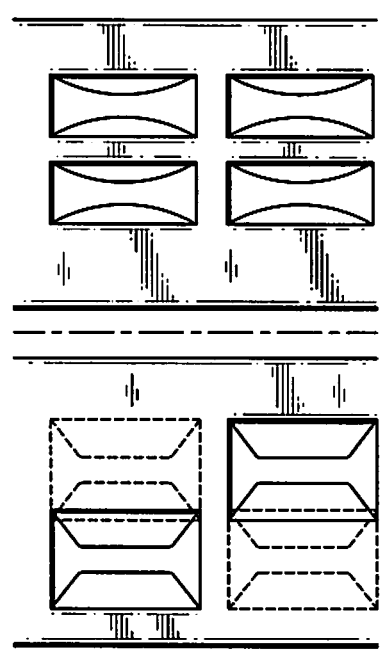
FIG. 1 is a top view of a portion of a conventional staple pocket arrangement on the anvil of a surgical stapler.
Figure 4:
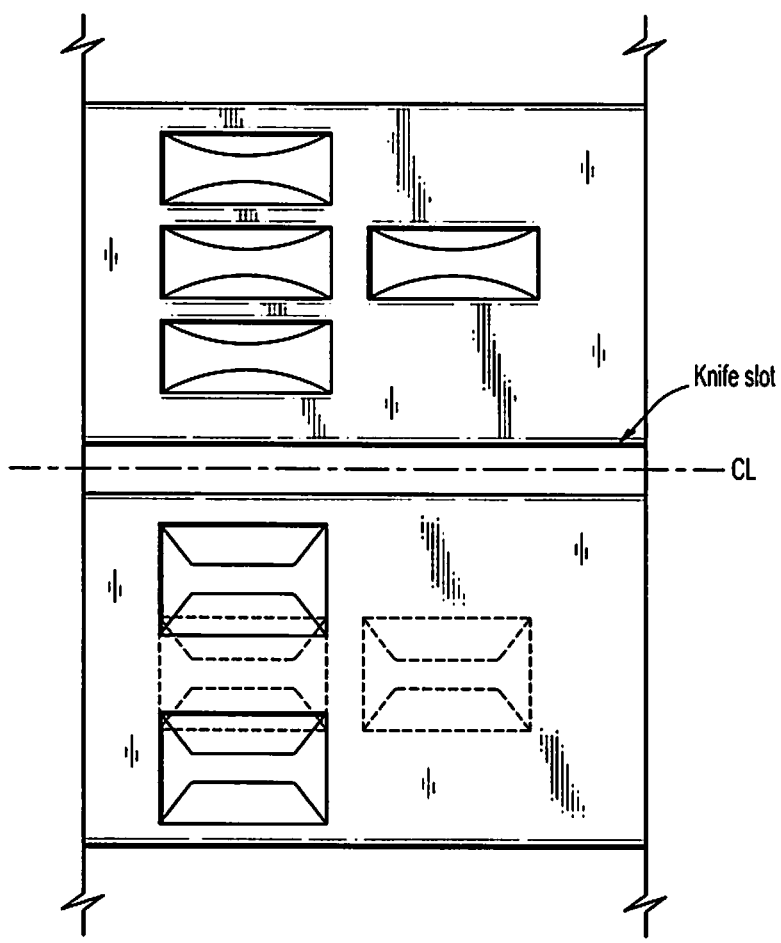
FIG. 4 is a top view of a portion of another conventional staple pocket arrangement on the anvil of a surgical stapler.
Figure 5:
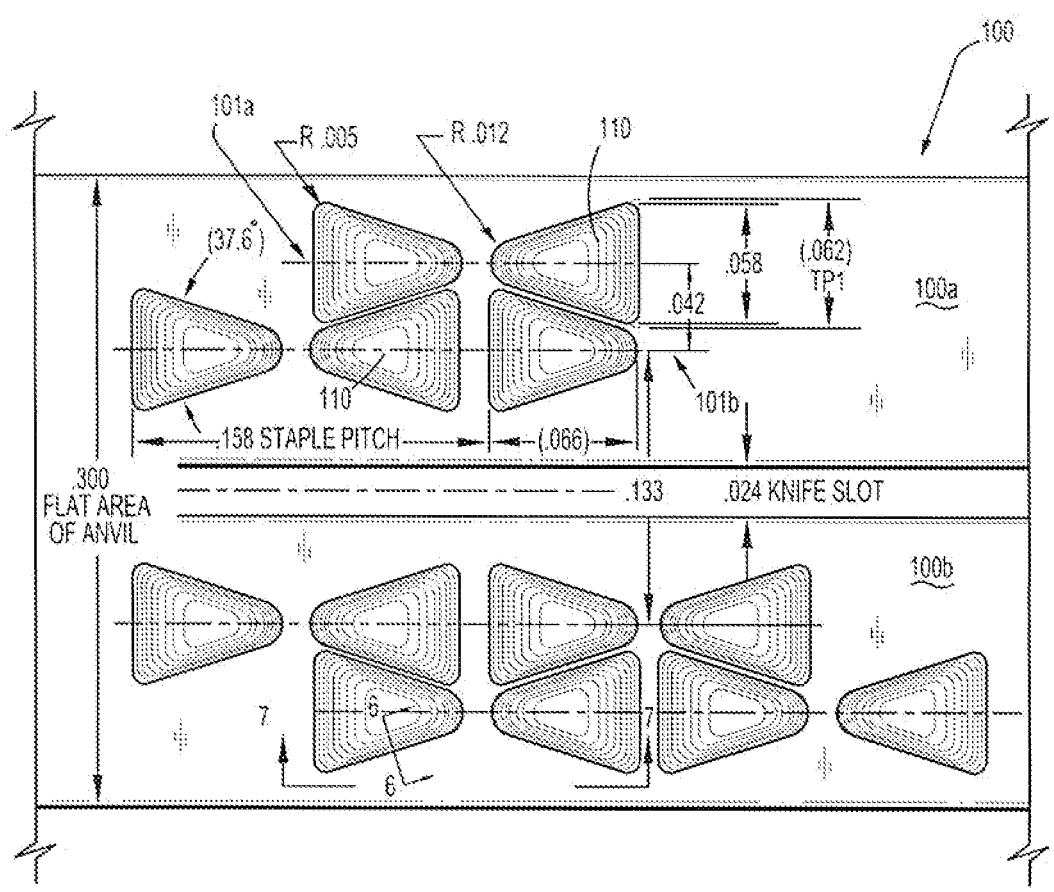
FIG. 5 is a top view of a staple pocket arrangement on the anvil of a surgical stapler, in accordance with an example embodiment of the present invention.

FIG. 5 is a top view of a staple pocket arrangement on the anvil of a surgical stapler, in accordance with an example embodiment of the present invention. Specifically, FIG. 5 illustrates an anvil surface 100 having a first side 100a and a second side 100b separated by a knife slot. On each of the first side 100a and the second side 100b of the anvil surface 100 there is defined two rows of staple pockets 110. Referring to the first side 100a of the anvil surface 100, a first row of staple pockets 110 has a center line 101a and a second row of staple pockets 110 has a center line 101b. For the purposes of clarity, only several staple pockets 110 have been shown. However, the anvil surface 100 may have any number of staple pockets 100 in each of the rows. Furthermore, while exemplary embodiments described herein include rows of staple pockets that are arranged adjacent to a knife slot, exemplary embodiments of the present invention maybe employed in connection with any type of surgical stapler, e.g., with or without a knife slot or any other structural feature.

The anvil surface 100 is arranged with pairs of staple pockets 110 corresponding to each staple to be closed. For instance, referring to the pair of staple pockets 110 arranged along the center line 101a, there is provided a distal staple pocket for receiving and closing a distal-most leg of a staple, and a proximal staple pocket for receiving and closing a proximal-most leg of a staple. The distal staple pocket 110 may be a mirror image of the proximal staple pocket 110.

The staple pockets 110 may have various shapes. As shown in FIG. 5, each staple pocket 110 may be roughly triangular in shape when viewed from above. Alternatively, each staple pocket 110 may have a shape when viewed from above that resembles a "bicycle seat", e.g., being generally triangular and having a series of convex and concave curves along its sides. Other shapes may also be employed.

Each respective staple leg is received at a longitudinal end of the staple pocket 110 that provides a relatively wide target area for receiving the staple leg. Since the staple pocket 110 is relatively wide at the longitudinal end at which the staple leg is received, the staple pocket arrangement may eliminate or at least minimize the likelihood that a staple leg will miss the staple pocket due to, e.g., misalignment between a first jaw of the surgical stapler having the anvil and a second jaw of the surgical stapler having a cartridge configured to fire the staples.

Figure 7:
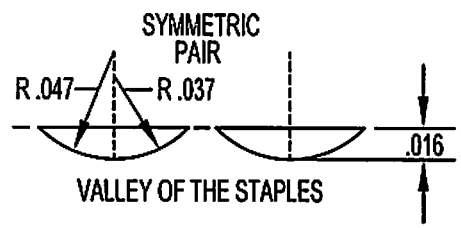
FIG. 7 is a cross-sectional view, taken along lines 7-7, of a portion of the staple pocket illustrated in FIG. 5.
Figure 6:
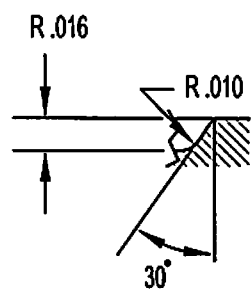
FIG. 6 is a cross-sectional view, taken along lines 6-6, of a portion of the staple pocket illustrated in FIG. 5.

Each of the staple pockets 110 is narrower at its opposite end, e.g., the end at which the staple leg emerges after being formed into an arc by the curved canyon of the staple pocket 110. The staple pocket 110 provides staple guidance in that the canyon walls along which a staple leg is guided are steeply angled for the entire wall (see, for instance, FIG. 6) so that the staple leg travels toward and along the center of the canyon and then up and out the far end narrow end of the canyon. The floor of the canyon has a generally smooth and continuous curvature which provides for the bending of the staple leg, as shown, for example, in FIG. 7. Alternatively or additionally, the floor of the canyon may have changing radii. The surfaces of the staple pockets are joined to each other with sufficiently large radii so as to eliminate or at least minimize tight corners that may snag or impede staple legs that are moving along the surface. Furthermore, the compound angle between these surfaces provides a sufficiently steep slide ramp for the staple legs to follow. The staples follow these slide ramps down into the canyon for proper bending or forming even when the staple is not well aimed by the cartridge.

Figure 8:
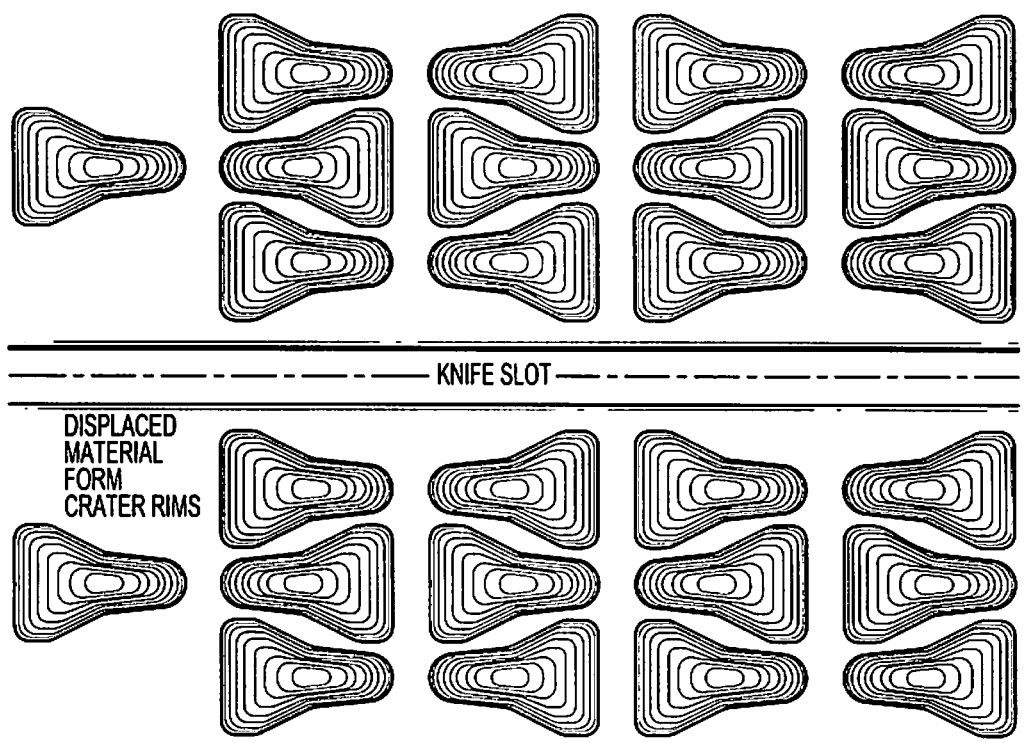
FIG. 8 is a top view of a staple pocket arrangement on the anvil of a surgical stapler, in accordance with an example embodiment of the present invention.
Figure 9:
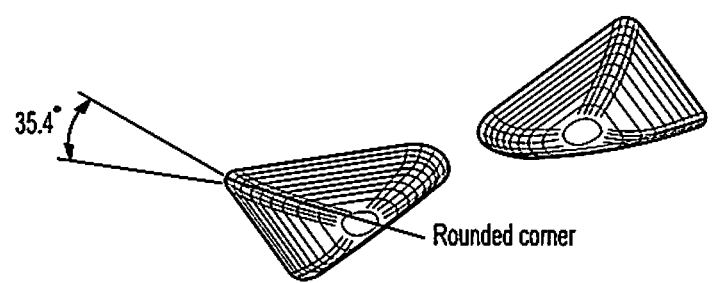
FIG. 9 is a bottom perspective view of another staple pocket arrangement on the anvil of a surgical stapler, in accordance with an example embodiment of the present invention.

Since this opposite end of the staple pocket 110 is relatively narrow, each staple pocket 110 in a first row of staple pockets 110 may be nested with a staple pocket from an adjacent row of staple pockets. Each row of staple pockets (and corresponding staples) may be longitudinally offset from another row, e.g., by approximately one half of the pocket-pair (or staple) center-to-center pitch. Thus, the proximal staple pocket of a first row nests with a distal staple pocket of a second row as shown in FIG. 5. In an example embodiment, see, for instance FIG. 8, a third row of staple pockets may be provided wherein the distal staple pocket of the second row also nests with the proximal staple pocket of the third row.

A series of staple pocket-pairs is formed in the anvil of a surgical stapling device. The number of staple pocket-pairs and their location depends upon the desired staple pattern desired. Typically, there will be several rows of pockets arranged alongside, e.g., parallel to, each other. For example, the sides of the staple pocket, e.g., those portions between the inner and outer longitudinal ends, may be angled relative to a center line of the row. In such an arrangement, when the staple pocket in the first row of staple pockets is nested with the staple pocket from the second row of staple pockets, adjacent sides of the staple pockets may be generally parallel to each other.

The section of tissue is clamped between the anvil and a cartridge loaded with staples. Each staple in the cartridge is generally aligned with a corresponding pair of staple pockets. Upon firing, the staples are pushed out of the cartridge so that the legs of the staples penetrate the section of tissue and proceed into the respective staple pockets. Continuous operation of the staple firing mechanism causes the staple legs to be received into the wide end of the staple pocket 110 and to slide along the curved valley of the pocket to bend or form in accordance with the curvature of the staple pocket. Eventually, the legs of each staple are fully bent or formed such that the section of tissue is held between the spine of the staple and the bent staple legs.

The surgical staple pocket arrangement may provide advantages over the staple pocket arrangements of conventional surgical stapler devices. For instance, the staple pocket arrangement hereof may provide an incoming staple leg capture area that is more tolerant of poorly aimed staples, e.g., that is able to receive and effectively bend a staple leg that is slightly mis-aligned relative to the center line of the staple pocket. This is due at least in part to the wide capture area located at the outer longitudinal end of the staple pockets and to the staple pockets' generally triangular shape. Thus, one feature of the staple pockets hereof is the provision of a wide capture area at one end of the staple pocket, which permits effective operation of the surgical stapler device even for staple legs arriving off-center due to a reasonable amount of misalignment between the anvil and the staple cartridge. Another feature hereof is that sharp corners which tend to snag the ends of staple legs are eliminated or at least minimized. Another feature hereof is that regardless of where the end of the staple leg arrives across the broad end of the pocket, there is a sufficiently steep slope or sliding angle so that the staple leg is induced to follow the forming curvature of the pocket. The steep sidewalls of the staple pocket function to guide the staple leg back towards the center of the staple as the staple leg gets bent or formed, regardless of off-center arrival of the staple leg. Rows of these pockets may be neatly nested alongside each other in close proximity, e.g., when phase shifted by approximately one half of the pocket-pair pitch. This nesting of the staple pockets of adjacent rows of staple pockets allows each staple pocket to have a greater staple capture area and permits adjacent rows of staple pockets to be spaced closer together.

In summary, the arrangement hereof may provide, relative to conventional staple pocket arrangements, a wider staple leg input capture area, a steeper slide angle to induce the staple to start forming, a shape that allows rows to be nested efficiently and an arrangement in which the radii of curvature of the staple pockets are broader than the radius of the staple wire. The staple pocket arrangement may eliminate or at least minimize sharp corners which may tend to snag staples. Thus, the staple pocket arrangement may be more tolerant of poorly aimed staples, makes more efficient use of space on the anvil and is less likely to cause a staple jam or buckling.

The staple pocket arrangement hereof may be formed by various manufacturing methods. For example, the staple pocket arrangement may be formed as described, e.g., in U.S. Provisional Patent Application No. 60/703,493, entitled "System and Method for Forming Staple Pockets of a Surgical Stapler", filed on Jul. 27, 2005, and in U.S. patent application Ser. No. 11/494,999, entitled "System and Method for Forming Staple Pockets of a Surgical Stapler," filed on Jul. 27, 2006, each of which is expressly incorporated herein in its entirety by reference thereto.

What is claimed is:

1. A surgical stapler device for closing staples, each staple having a distal staple leg and a proximal staple leg, the device comprising:
    an anvil portion including at least two rows of staple pockets, each one of the at least two rows including a staple pocket set corresponding to each staple, each staple pocket set including a distal staple pocket for receiving and forming the distal staple leg of the corresponding staple and a proximal staple pocket for receiving and forming the proximal staple leg of the corresponding staple, wherein at least a portion of a staple pocket of a staple pocket set from a first row of staple pocket sets is disposed in a region between the staple pockets of a staple pocket set from a second row of staple pocket sets,
    wherein a first space is defined between each staple pocket set and a second space is defined between the distal staple pocket and the proximal staple pocket of each staple pocket set so that the distal staple pocket and the proximal staple pocket are free from contact with one another, and
    wherein at least one proximal staple pocket of a first row of staple pocket sets is transversely aligned with at least one distal staple pocket of a second row of staple pocket sets.

2. The surgical stapler device of claim 1, wherein the staple pocket sets of the first row are longitudinally offset from the staple pocket sets of the second row.

3. The surgical stapler device of claim 2, wherein the staple pocket sets of the first row are longitudinally offset from the staple pocket sets of the second row by one half of a center-to-center pitch of a staple pocket set.

4. The surgical stapler device of claim 2, each staple pocket has a generally triangular shape foot print.

5. The surgical stapler device of claim 1, wherein, in each row of the at least two rows, the staple pocket sets are arranged along a center line.

6. The surgical stapler device of claim 5, wherein, in each staple pocket set, a first one of a distal and a proximal staple pocket is a mirror image of a second one of the distal and the proximal staple pocket.

7. The surgical stapler device of claim 1, wherein, for each staple pocket set, an axially distal end and an axially proximal end of the staple pocket set is transversely wider than an axially central portion of the staple pocket set.

8. The surgical stapler device of claim 7, wherein the axially distal and proximal ends of each staple pocket set is configured to first receive a respective staple leg.

9. The surgical stapler device of claim 8, wherein each staple pocket of the staple pocket set includes a curved canyon floor configured to form a respective staple leg into an arc as the staple leg is received and pushed into the curved canyon floor of the respective staple pocket.

10. The surgical stapler device of claim 9, wherein each staple pocket includes walls along which a staple leg is guided, the walls being steeply angled with respect to a tissue contact surface.

11. The surgical stapler device of claim 9, wherein the canyon floor has a generally smooth and continuous curvature.

12. An anvil, comprising:
    at least two rows of staple pockets, each one of the at least two rows including a staple pocket set, each staple pocket set corresponding to a single staple and including a distal staple pocket and a proximal staple pocket, wherein a staple pocket in a first row of staple pocket sets is nested with a staple pocket from a second row of staple pocket sets, each staple pocket including a first absolute end and a second absolute end, the first and second absolute ends being disposed on opposed ends of the staple pocket,
    wherein a first space is defined between each staple pocket set and a second space is defined between a first location defined by one of the absolute ends of the distal staple pocket and a second location defined by one of the absolute ends of the proximal staple pocket of each staple pocket set, the first and second locations being disposed adjacent one another, and
    wherein each proximal staple pocket of a staple pocket set of a first row of staple pockets is axially transversely off-set with respect to a respective proximal staple pocket of a staple pocket set of a second row of staple pockets.

13. The anvil of claim 12, wherein the staple pocket sets of the first row are longitudinally offset from the staple pocket sets of the second row.

14. The anvil of claim 12, wherein each staple pocket has a generally triangular shape.

15. The anvil of claim 14, wherein, in each staple pocket set, a distal staple pocket is a mirror image of a proximal staple pocket.

16. The anvil of claim 14, wherein each staple pocket includes walls that are steeply angled with respect to a tissue contact surface.

17. A surgical stapler device for forming staples, the surgical stapler supporting a plurality of unformed staples in a cartridge portion such that each staple has a distally disposed staple leg and a proximally disposed staple leg, the surgical stapler device comprising:

an anvil portion defining at least a first row and a second row of longitudinal extending staple forming pocket sets, each staple forming pocket set including a first staple pocket and a second staple pocket, wherein a first space is defined between each staple pocket set and a second space is defined between the first staple pocket and the second staple pocket of each staple pocket set, the second spaces of each respective row being aligned along a central axis extending centrally through the staple pockets of the respective row, wherein each row of staple pocket sets defines a respective transverse width dimension, and wherein the first row of staple pocket sets is nested in the second row of staple pocket sets such that a transverse width dimension of the combined first and second rows of staple pocket sets is less than or equal to a sum of the transverse width dimension of the first row of staple pocket sets and the second row of staple pocket sets.

18. The surgical stapler device of claim 17, wherein each row of staple pocket sets defines a first side edge and a second side edge, and wherein the first side edge of the first row of staple pocket sets is closer to an axial center line of the second row of staple pocket sets as compared to at least one of the first and second side edges of the second row of staple pocket sets.

19. The surgical stapler device of claim 17, wherein each staple pocket of each staple pocket set has a substantially triangular shaped perimetrical profile.

20. The surgical stapler device of claim 17, wherein each staple pocket of each staple pocket set has a substantially tear-drop shaped perimetrical profile.

21. The surgical stapler device of claim 20, wherein each staple pocket of each staple pocket set defines an apex, and wherein the apex of each staple pocket of each staple pocket set is adjacent to one another.

22. The surgical stapler device of claim 21, wherein the apex of each staple pocket is disposed substantially along a longitudinal center line of each staple pocket set.

* * * * *